United States Patent
Yu et al.

(10) Patent No.: US 6,248,373 B1
(45) Date of Patent: Jun. 19, 2001

(54) ENZYMATIC MODIFICATION OF PSYLLIUM

(75) Inventors: Liangli Yu, West Lafayette, IN (US); Gwen E. DeVay, Battle Creek, MI (US); Grace H. Lai, Portage, MI (US); Curtis T. Simmons, Kalamazoo, MI (US); Susan R. Neilsen, Battle Creek, MI (US)

(73) Assignee: Kellogg Company, Battle Creek, MI (US)

( * ) Notice: Subject to any disclaimer, the term of this patent is extended or adjusted under 35 U.S.C. 154(b) by 0 days.

(21) Appl. No.: 09/326,045

(22) Filed: Jun. 4, 1999

Related U.S. Application Data

(60) Provisional application No. 60/088,313, filed on Jun. 5, 1998.

(51) Int. Cl.[7] .................................................. A23B 9/28
(52) U.S. Cl. ................. 426/52; 426/53; 426/590
(58) Field of Search .................... 424/195.1; 514/54; 426/49, 50, 51, 52, 53, 28, 615, 635, 590, 569; 435/72, 74, 96, 99

(56) References Cited

U.S. PATENT DOCUMENTS

| Re. 32,811 | 12/1988 | Rudin ................................ 424/195.1 |
| 4,488,975 * | 12/1984 | Almond ........................... 252/8.55 R |
| 4,857,339 | 8/1989 | Maselli et al. ........................... 426/28 |
| 4,999,200 | 3/1991 | Casillan ................................ 424/480 |
| 5,061,497 | 10/1991 | Thacker et al. ........................ 426/31 |
| 5,106,634 | 4/1992 | Thacker et al. ........................ 426/31 |
| 5,225,219 | 7/1993 | Inglett .................................... 426/28 |
| 5,266,473 | 11/1993 | Nielsen ................................ 435/219 |
| 5,651,988 | 7/1997 | Olinger et al. ....................... 424/489 |

OTHER PUBLICATIONS

Lee et al. Journal of ADAC Int'l—vol. 78, No. 3, 1995 entitled Determination of Soluble and Insoluble Dietary Fiber in Psyllium–Containing Cereal Products.

Chan—A Forgotten Natural Dietary Fiber: Psyllium Mucilloid—Cereal Foods World 919–922, vol. 33. No. 11, Nov. 1988.

Fernandes, "Psyllium—It's Role in a Heart Healthy Diet (1997)".

Arjmandi, "Soluble Dietary Fiber and Cholesterol Influence In Vivo Hepatic and Intestinal Cholesterol Biosynthesis in Rats"—1559–1545 American Institute of Nutrition (1992).

Pons, Review Paper "Instrumental Texture Profile Analysis with Particular Reference to Gelled Systems" Journal of Texture Studies 27(1996) 597–624.

* cited by examiner

*Primary Examiner*—Keith Hendricks
(74) *Attorney, Agent, or Firm*—Howard & Howard

(57) ABSTRACT

Enzymatic treatment of raw psyllium yields a modified psyllium with improved functionality. A preferred method includes the steps of adding raw psyllium to an aqueous dispersion containing a sufficient amount of an enzyme capable of modifying the carbohydrates of the raw psyllium to yield a modified psyllium with improved functionality. Products containing the modified psyllium and methods for producing the same are also provided.

19 Claims, No Drawings

ENZYMATIC MODIFICATION OF PSYLLIUM

This application claims the benefit of provisional application No. 60/088,313, filed Jun. 5, 1998.

BACKGROUND OF THE INVENTION

The present invention relates to methods for modifying psyllium with a psyllium modifying agent to improve and extend the functionality of the psyllium. In a preferred embodiment, the psyllium modifying agent is an enzyme. The resultant modified psyllium has improved manufacturing qualities that is prepared from raw psyllium. More particularly, the modified psyllium of the present invention has, e.g. a decreased gel hardness compared to that of the raw psyllium starting material, and in preferred embodiments a 5% w/v suspension of modified psyllium in water does not gel at all or gels to an insubstantial degree.

The present invention also relates to food products containing the modified psyllium, methods for preparing the food products, and methods treating a patient by administering the modified psyllium of the invention to the patient, e.g. to lower serum cholesterol.

Psyllium is a mucilaginous material derived from seeds from the plants of the Plantago genus, which grows in certain sub-tropical regions. *Plantago ovata* is a preferred species and is commercially grown in India. The seeds of Plantago sp. are dark brown, smooth, boat shaped and shiny. Psyllium seed is used in whole, ground or dehusked form to make a variety of psyllium containing products.

Starches are among the polysaccharides that naturally occur in plants, including psyllium. Starches are polysaccharides that naturally occur in grains and other plants, and serve as a permanent food store for the plant. Starch includes two structurally different polysaccharides, amylose and amylopectin. Amylose is a linear molecule composed of 250–300 D-gluco-pyranose units uniformly linked by alpha-1,4 glucosidic bonds. Amylopectin consists of 1000 or more glucose units that are also connected with alpha-1,4 glucosidic bonds, but also has a number of branch attached to the main chain by alpha-1,6 glucosidic bonds.

It is known to use enzymes, particularly glucanases, to modify the starches in various farinaceous grains to obtain more desirable polysaccharides. Amylases are enzymes that hydrolyze the alpha-1,4 bonds. Alpha-amylases hydrolyze starch by random splitting of these bonds. β-amylases can only hydrolyze the alpha-1,4 linkages of amylopectin until a branch point is approached because the enzyme cannot hydrolyze alpha-1,6 bonds, leaving dextrins as a byproduct. U.S. Pat. No. 5,225,219 to Inglett describes a process for producing amylodextrin compositions from the starches of various substrates, e.g. cereal grains, by hydrolysis with an alpha-amylase.

However, it is not the starches of psyllium that relate to the poor functional qualities of psyllium, but other polysaccharides such as the soluble and insoluble fibers. Psyllium husk, an excellent source of both soluble and insoluble fibers, and has a proven cholesterol-lowering effect. There are two main types of known dietary fibers broadly classified as soluble fibers and insoluble fibers. Generally, insoluble fibers are recognized for their bulk laxative effect, while soluble fibers are known to have a cholesterol-lowering effect. Psyllium seed, particularly the psyllium husk, and certain other grains, particularly oats, contain both soluble and insoluble fibers, and are commercially available in various foods and pharmaceuticals.

Psyllium seed husk has a soluble fiber content approximately eight times greater than that of the soluble fiber content of oat bran, and thus there is great interest in psyllium for its beneficial health effects. These beneficial health effects include reducing serum total cholesterol, reducing low density lipoprotein cholesterol, lowering glycemic index and lipid levels, affecting fecal and colonic microbial metabolism, and for treatment of intestinal disorders.

Psyllium contains both neutral and acidic polysaccharides. Psyllium from different Plantago species vary in monosaccharide composition and content. These monosaccharides include D-xylose, D-arabinose, D-rhamnose, D-galactose, D-galacturonic acid, 4-O-methyl-D-glucuronic acid, and 2-O-(2-D-galactopyranosyluronic acid)-L-rhamnose (1,2,3,4,5). Kennedy et al. have reported detailed structural data for *Plantago ovata*. See, e.g., Kennedy et al., Structural datafor the carbohydrate of ispaghala husk ex plantago ovata forsk, Carbohydrate Research 75:265–274 (1979). Methylation analysis and partial acidic hydrolysis have shown that the mucilage polysaccharide is a highly branched acidic arabinoxylan. The xylan backbone has both (1→44) and (1→3) linkages. Substitutent groups, including rabinose, xylose, and 2-O-(galactopyranosyluronic acid)-rhamnose, are attached to the arabinoxylan chain by (1→2) and (1→3) linkages.

Psyllium husk can absorb as much as 90 times its weight in water and forms a viscous gel upon hydration. These properties are problematic to the preparation of psyllium-containing products. The mucilaginous nature of psyllium leads to an undesirable slimy or adhesive texture and mouthfeel upon hydration. This slimy mouthfeel is unpalatable and various attempts have been made to mask these undesirable characteristics.

The aforementioned difficulties become particularly troublesome when formulating beverages or drink mixes. Leis, Jr. and others have attempted to overcome some ofthe problems associated with a bulk laxative powdered drink mix preparation by using a raw psyllium having a specific particle size range as described in U.S. Pat. Nos. 5,445,831 and 5,149,541.

Barbera et al. describe the inclusion of an amount of an edible acid, e.g. citric acid, high enough to slow the gelation rate but below a level that the edible acid is a flavorant to prevent agglomeration ofpsyllium of aparticularparticle size range, e.g. as described in U.S. Pat. Nos. 5,234,687, 5,219, 570 and 5,425,945.

U.S. Pat. No. 4,551,331 and its U.S. Reissue No. 32,811 describe a modified dry dietary fiber product, wherein a dietary fiber such as psyllium is coated with from 0.5 to 20% by weight of a food grade emulsifier. U.S. Pat. Nos. 44,459, 280 and 4,548,806 to Colliopoulos et al. also attempt to alleviate agglomeration caused by psyllium gelation by coating psyllium with a hydrolyzed starch oligosaccharide such as maltodextrin, which may also function as an emulsifying agent.

It is known that several other variables can be controlled to inhibit psyllium hydration. These variables include formation of nuggets by extrusion as described in U.S. Pat. No. 5,227,248. Changes in pH or particle size, competition of other food ingredients for water (e.g. sugar), or addition of citric acid have previously been used to improve the handling properties of psyllium.

Additionally, the U.S. Food and Drug Administration (USFDA) requires a considerable amount of psyllium must be included in a food product before a health claim can be made for reducing serum cholesterol, i.e. the amount of psyllium to be included is generally about 10 g/day, which provides approximately 7 g of soluble fiber/day.

Drink mixes are apreferred psyllium delivery system, but suitable drink mixes containing such an amount of psyllium cannot be made using raw psyllium. Therefore, psyllium containing beverages generally deliver 3.4 g of psyllium, approximately one-third ofthe required daily dose. Therefore, the consumer must imbibe three 8 oz. psyllium-containing beverages/day to ingest the required daily dose.

It has been widely accepted that pH can alter the functionality of a polysaccharide by influencing the molecular charges. The changes ofmolecular charges subsequently influence the interactions between solutes and lead to an alteration of food functionality. It has been shown that the rate of psyllium hydration in a psyllium-containing suspension can be reduced by adjusting the pH of a psyllium-containing suspension. The influence of particle size on the polysaccharide hydration has also been established. Similar to most polysaccharides, psyllium with a smaller particle size has a greater hydration rate. The competition of other ingredients, such as salt and sugar, have been observed to reduce psyllium polysaccharide hydration, including the polysaccharides found in psyllium.

Difficulties notwithstanding, the desirable therapeutic effects provided by psyllium have led to many prior art psyllium-containing formulations. For example, various psyllium-containing foods have been proposed which purport to take advantage of the natural digestion regulation properties of psyllium, or the satiating effect of psyllium, e.g. as described in U.S. Pat. Nos. 3,574,634 and 4,348,379. U.S. Pat. No. 5,266,473 describes the enzymatic treatment of psyllium with certain proteases to alleviate problems associated with psyllium allergenicity.

There is a need in the art to overcome the manufacturing and handling difficulties associated with psyllium. The present invention relates to enzymatically treated psyllium and is described in detail below.

SUMMARY OF THE INVENTION

The present invention provides a method for preparing modified psyllium by treating raw psyllium with a non-starch psyllium polysaccharide modifying agent, e.g. an acid or an enzyme, to produce a modified psyllium with improved or desirable functional properties compared to that of raw psyllium. Preferably, the modified psyllium is prepared by enzymatically treating psyllium to improve certain qualities for subsequent use in the manufacture of, e.g. foodstuffs and pharmaceuticals. The resultant product has improved processing qualities compared to untreated raw psyllium. For purposes of the present invention, the term "raw psyllium" as used herein is meant to include psyllium husk or any other product that contains psyllium husk or is derived from psyllium husk, e.g. whole psyllium seed, psyllium flour, isolated psyllium husk polysaccharides such as the soluble or insoluble fibers or mixtures thereof, etc. Commercially available 40 mesh raw psyllium is suitable for preparing the modified psyllium of the present invention.

In apreferred embodiment, the enzymatically modified psyllium is produced by preparing a buffered aqueous mixture of raw psyllium and an effective amount of an enzyme capable of modifying the non-starch polysaccharides of raw psyllium under conditions, e.g. temperature or pH, wherein the enzyme modifies said non-starch polysaccharides of the raw psyllium.

In a particularly preferred embodiment, raw psyllium is treated with the enzyme for a sufficient period of time to reduce the rate of water absorption of the resultant enzymatically modified psyllium compared to that of the raw psyllium starting product. The time period may range from about 1 hour to seven days or even greater, depending upon processing conditions and the desired properties ofthe end product. Typically, the reaction time will range from about 2 to about 24 hours.

In another preferred embodiment, enzyme is added to a slurry of psyllium and buffer and incubated, that is enzymatically reacted or treated for a period of time sufficient to render the resultant enzymatically treated product with the desired physical and chemical, which will vary with the intended end use. The enzyme is preferably an enzyme that will react with the insoluble or soluble fibers in the psyllium to impart the desired physical characteristics to the final product. Preferred enzymes are capable of breaking the xylan backbone, e.g. xylanases. A preferred buffer is an acetate buffer.

Once the desired endpoint is reached, the enzymes may be inactivated, e.g. by heating or acidification. The mixture may then be directly used in preparing a final product, or subjected to freeze drying to yield the enzymatically modified psyllium product. The modified psyllium may then be used in other applications, e.g. preparation of psyllium-containing food products, animal feed, pharmaceuticals and the like. These end products will be prepared according to art-known techniques, e.g. blending, extrusion, mixing, heating, drying, etc. In general, the final product will be prepared by incorporating the modified psyllium with other edible ingredients, e.g. flours, eggs, sugars, water, flavorants, etc. and further processed using art-known techniques to achieve the final product.

In an alternative embodiment of the invention, the raw psyllium may be enzymatically modified as a direct step in the manufacture of a final modified psyllium-containing product. For example, a preferred embodiment of the invention is directed to a method of preparing a psyllium- containing food product by blending raw psyllium with at least one edible ingredient, e.g. flour, water, eggs, etc. to form a blend; and adding an effective amount of an enzyme capable of modifying the non-starch polysaccharides of raw psyllium to the blend under conditions wherein the enzyme modifies the non-starch polysaccharides of the raw psyllium to yield an intermediate or final food product having improved qualities compared to the same or substantially similar product prepared with unmodified raw psyllium. Thus, if one desires to prepare a psyllium-containing pasta, one can first form a dough containing raw psyllium, and enzymatically modify the raw psyllium that is in the dough, eliminating the need to prepare modified psyllium prior to incorporation with other edible ingredients. This method allows formation of the modified psyllium in situ rather than by separate manufacture, which may be desirable in certain instances.

The enzymes may also react on other ingredients in such a mixture and can be controlled in such a manner, e.g. by regulating temperature and reaction time, using enzymes of different purity, altering the ratios of the components, and the like.

The enzymatically modified psyllium product of the invention may include the enzyme or enzyme components, i.e. denatured or otherwise inactivated enzyme. The final modified psyllium product may also include byproducts of the enzymatic action on the psyllium, e.g. the various mono- di- and polysaccharides that may result from enzymatic treatment. The composition of the final product will depend on recovery methods used, e.g. freeze drying, air drying, filtration, centrifugation, and the like. The enzyme-psyllium mixture may also be directly added to other food components, eliminating the need for isolating the enzymatically modified psyllium.

In comparison to untreated psyllium, the enzymatically treated psyllium of the present invention has a modified water uptake rate, gel hardness and adhesiveness. These functional properties may be either increased or decreased depending on the end result. Generally, it is preferred to decrease gel hardness for most food functions, and to eliminate gel formation for certain beverages. Increased gel hardness or increased viscosity may be desirable, for example, when a viscous formulation is needed to maintain the particulate matter in suspension, e.g. a beverage containing particles of insoluble salts of vitamins. Preferably, the enzymatically modified psyllium retains substantial portion of its original insoluble and soluble fiber contents. Thus, the psyllium according to the present invention can be substituted for raw or otherwise treated, e.g. pregelatinized psyllium to prepare improved food and pharmaceutical products compared to those of the prior art. It will be understood that the modified psyllium may also contain various byproducts of the reaction between the solution and the psyllium, e.g. mono-, di-, poly- and oligo-saccharides and the like that result from the treatment of the raw psyllium. The recovered modified psyllium may be directly added with other ingredients to prepare the desired end product, e.g. a psyllium-containing food product, or may be dried or freeze dried and stored for later use. Byproducts may also be isolated from the solution mixture and used as a separate ingredient or in another application as desired.

Other embodiments of the present invention will become apparent in the foil description of the invention and examples of preferred embodiments of the invention.

DETAILED DESCRIPTION

The modified psyllium of the present invention may be prepared by reacting raw psyllium with a polysaccharide modifying agent that is capable of modifying the non-starch polysaccharides of psyllium under conditions such that polysaccharide modification can take place. Suitable polysaccharides include enzymes and acids, such as the acids described in co-pending U.S. application Ser. No. 09/325,959 filed June 4, 1999 entitled ACID AND SOLVENT MODIFICATION OF PSYLLIUM, which is hereby incorporated by reference.

The enzymatically modified psyllium of the present invention may be prepared by enzymatically treating raw psyllium with an enzyme capable of breaking β-glycosidic linkages found in psyllium polysaccharides. The enzyme is preferably added to a slurry of psyllium and buffer solution, and incubated for a period of time sufficient to impart the desired physico-chemical properties into the psyllium. The enzymatic modification can also be performed during preparation of food products, e.g. by adding enzyme into a psyllium-containing dough to improve the final food product.

The psyllium used as the starting material is preferably raw psyllium husk. Preferably, the psyllium is 98% pure, because this grade of psyllium is especially suited for use in the food and pharmaceutical industries. It may be preferable in certain instances to use a less pure psyllium, e.g. 85% pure, particularly if the end product will be used as a feed for farm animals. Thus, the starting product will vary with the end use of the final product.

The enzymes of the present invention are preferably those that are capable of breaking or otherwise modifying the xylan backbone found in the non-starch polysaccharides in psyllium, e.g. fibers. In preferred embodiments, the enzymes of the present invention are capable of breaking β-linkages found in the non-starch polysaccharides of psyllium, e.g. by hydrolysis. Preferred enzymes include cellulases, xylanases, hemicellulases, pentosanses, aribanases, β-glucanases, and mixtures thereof. It is also preferred that the enzymes are substantially free of amylase and protease activities. The skilled artisan will understand that enzymes are not always pure but are usually mixtures of enzymes, with the enzyme of the preferred activity constituting the major proportion of the enzyme. These impurities, i.e. undesired enzymes, may be present despite careful control and extraction, but preferably constitute only a minor proportion of the mixture.

Examples of commercially available enzymes that may be used in accordance with the present invention include Viscozyme L, Shearzyme L, Pentopan Mono BG and Celluclat 1.5L, all of which are commercially available from Novo North America, Inc.

Viscozyme L provides xylanase, arabinase, cellulase, β-glucanase, and hemicellulase activities. Shearzyme L is a highly purified xylanase, substantially free of amylase and protease activities. Pentopan Mono BG is a purified β-1,4-xylanase (pentosanase), and Celluclat 1.5L is a cellulase.

Each of the enzymes has a preferred reaction temperature, which generally ranges from about 40 to about 60° C. The operation (incubation) temperature may vary over a wide range depending on the enzyme. For example, thermostable enzymes are operative over a generally higher range of temperature than other enzymes. Thus, the reaction temperature will vary with the enzyme or enzymes used.

Additionally, the pH of the slurry should be adjusted to a pH at which the enzyme is active, if necessary. Buffer solutions will be selected in accordance with many factors, including the selected enzyme. Preferably the pH is from 4.5 to 6. The skilled artisan will understand that optimal pH will vary according to many factors, e.g., the selected enzyme(s), the preferred rate of reaction, and other conditions apparent to the skilled artisan.

Preferred buffer systems include acetate, phosphate, carbonate, bicarbonate, pyrophasphate, tartaric acid, citrate and the like.

Compounds or substances which are required or that facilitate enzymatic action may also be included, e.g. calcium ions (usually provided as a calcium salt), etc.

Reaction times will also vary with the selected enzyme and other conditions, e.g. pH, temperature, the buffer system used, etc. Generally, a reaction time of from about 0.5 to 24 hours is sufficient to yield a suitable modified psyllium product. Temperature, enzyme concentration and other variables known to the skilled artisan will all determine the optimum reaction time for particular enzymes.

After incubation, the enzyme is inactivated. Inactivation may be accomplished via any means known in the art, e.g. by acidification or other adjustment of the pH; by microwave radiation or by heat inactivation.

After inactivation, the reaction mixture is freeze dried to obtain the modified psyllium product. Freeze drying may be accomplished by subjecting the slurry to temperatures of below freezing, e.g. −20° C. for a period of from about 2 to about 14 days. After freeze drying, it is preferred that the resultant modified psyllium product is milled or sieved to an appropriate particle size. The particle size will vary with the intended use of the modified psyllium. For example, larger particles of psyllium, e.g. those with a greater particle size than 80 mesh, e.g. 60 to 20 mesh, may be appropriate for a bulk laxative formulation, while smaller particles, e.g. 80 to 200 mesh or smaller, may be preferred for baked products such as muffins, or beverages and drink mixes. It is contemplated that particular size ranges or particle size distributions may be particularly useful in the production of particular products, and such particle size distributions are considered to be encompassed within the scope of the present invention.

The present invention is also directed to reducing serum cholesterol inducing LDL;

reducing serum triglycerides, and providing a bulk laxative effect in mammals. This is accomplished by orally administering a therapeutically effective amount of the enzymatically modified psyllium of the present invention to a mammal. The therapeutically effective amount is the amount needed to achieve the desired effect, e.g., a sufficient amount to lower serum cholesterol, a sufficient amount to lower serum LDL, a sufficient amount to lower serum triglycerides, or a sufficient amount to provide a bulk laxative effect. Preferably the mammal is a human.

The enzymatically modified psyllium of the present invention product of the present invention provides significant functional advantages over raw psyllium.

DETAILED DESCRIPTION OF THE PREFERRED EMBODIMENTS

General Procedure for Enzyme Modification of Psyllium

Twenty (20) grams of raw psyllium (98% purity, 40 mesh, commercially available from JB Laboratories) was mixed with 400 to 450 mls acetate buffer (50 mM, pH 4.8) or a different buffer having the same buffer capacity to form a slurry. Certain units of individual enzymes were then added and mixed into the slurry. The mixture was then incubated for about 1 hour in a water bath while shaking at a rate of 60 shakes/min at the optimal temperature for the selected enzyme. The enzymes were then inactivated by heating in a water bath or microwave. The reactants were then cooled to ambient temperature. After cooling, the slurry was transferred to a tray and freeze dried. The freeze drying process was conducted with a Genesis-25EL freeze dryer (commercially available from The Virtis Company, Gardiner, N.Y.) with a temperature program as follows: −40° C. for 12 hrs, −20° C. for 12 hrs; 0° C. for 12 hours; 10° C. for 12 hours; 20° C. for 12 hours; and 25° C. for 12 hours.

The freeze dried product is then sieved through a 1 mn sieve using a Wiley Mill Grinder (Model ED-5, commercially available through the Arthur H. Thomas Co., Phila., Pa.).

CONTROL EXAMPLE A

Control of the enzymatic modification was performed using above procedure without addition of the enzyme. The incubation was carried out at 50–55° C., followed by heating at 90° C. for 15 min. The resultant control paste was then freeze dried as described above.

Example 1

Two hundred and forty (240) units of Viscozyme L (commercially available from Novo North America, Inc.) was added to the psyllium slurry. This enzyme contains 100 FBG/g with a density of 1.2. Viscozyme L contains xylanase, arabinase, cellulase, β-glucanase, and hemicellulase activities. The incubation temperature was 45–50° C., and the enzyme was inactivated by heating at 80° C. for 15 minutes.

Example 2

The procedure of Example 1 was followed, except that 1200 units of Viscozyme L was added.

Example 3

Two thousand (2000) units of Shearzyme L (commercially available from Novo North America, Inc.) was added into the psyllium slurry. This enzyme contains 500 Fungal Xylanase Units (FXU) per gram (500 FXU/g) with a density of 1.1–1.2 g/ml. The enzyme is a purified xylanase, substantially free of amylase and protease activities. The incubation temperature was 45–50° C., and the enzyme was inactivated by heating at 90° C. for 15 minutes.

Example 4

Four thousand (4000) units of Shearzyme L was used in the method of Example 3.

Example 5

Six hundred (600) units of Pentopan Mono BG (commercially available from Novo North America, Inc.) was added to the psyllium slurry. Pentopan Mono BG contains 2500 FXU/g. The enzyme is a purified endo 1,4-xylanase (pentosanase). The incubation temperature was 52–55° C., and the enzyme was inactivated by microwave heating for 3 minutes.

Example 6

Two thousand five hundred (2500) units of Celluclat 1.5L, a cellulase commercially available from Novo North America, Inc., was added into the psyllium slurry. This enzyme contains 1500 NCU/g (NCU is a Novo Cellulase Unit). The incubation temperature was 45–50C, and the enzyme was inactivated by heating at 70° C. for 15 minutes.

Example 7

One hundred and ten (110) units of Shearzyme L were added to the psyllium slurry using the method described in Example 3.

Example 8

Five hundred (500) mg Xylanase 200 (commercially available from Enzyme Development Corporation, New York, N.Y.) were added to the psyllium slurry. The reaction mixture was incubated at 45–48° C. The enzyme was then inactivated by heating at 80° C. for 15 minutes.

Example 9

Analytical Methods for Modifications of Psyllium

Two tests, including water uptake rate and gelling properties, were performed to evaluate the functionality of enzymatically modified psyllium. In addition, fiber contents (both soluble and insoluble fiber) were measured, since soluble fiber might be associated with health benefits of psyllium, especially for laxative and hypocholesterol effects.

Water absorbing capacity was determined gravimetrically according to the previous method described by Elizalde et al., Empirical model for water intake and hydration rate of food powders by sorption and Baumann methods, *Journal of Food Science* 61: 407–409 (1996), with some modification. Briefly, all samples were equilibrated in a 10% relative humidity (RH) chamber for 48 hours. Then, samples were transferred into a 65% RH chamber and exposed to moisture for 5 min. The dry matter and the absolute amount of absorbed water were determined. All measurements were made in triplicate. The results were expressed as "mean±SD" in mg water absorbed by per gram of psyllium per minute (mg/g/min).

Gelling properties were analyzed using a TA-XT2 texture analyzer (Texture Technologies Corp., Scarsdale, N.Y.) with a 1 inch diameter probe. Texture profile analysis of heat-formed gels and cakes prepared with low cholesterol egg yolk concentrations as described in *Journal of Food Science* 62: 208–211. Analysis samples were prepared by adding 2.50g of psyllium into a beaker containing 50 ml distilled deionized water and stirred for 30 seconds. After setting at room temperature for 3 hours, gel samples were subjected to a single compression test. Measurements were performed with a pretest speed of 2.0 mm/sec, a test speed of 5.0 mm/sec, a post test speed of 5.0 mm/sec, and a distance of 6 mm. All measurements were made in triplicate. The results were expressed as "mean±SD" in gram force for gel hardness and adhesiveness. All results are shown in Table 1 below:

TABLE 1

| Example No. | Soluble Fiber (%) | Insoluble Fiber (%) | Water uptake rate (mg/g/min) | Hardness (g) | Adhesiveness (g) |
|---|---|---|---|---|---|
| Control A | 71.63 | 12.29 | 2.7 ± 0.21 | 94.54 ± 2.34 | 9.62 ± 0.89 |
| 1 | 56.65 | 12.35 | 2.33 ± 0.22 | 55.61 ± 1.01 | 2.54 ± 0.56 |
| 2 | 45.48 | 10.45 | 1.53 ± 0.09 | 29.58 ± 2.83 | 0 |
| 3 | 66.91 | 12.43 | 1.99 ± 0.6 | 72.71 ± 0.22 | 7.40 ± 2.22 |
| 4 | 59.05 | 11.09 | NA | 48.14 ± 1.15 | 6.02 ± 0.91 |
| 5 | 74.44 | 13.87 | 2.52 ± 0.10 | 122.11 ± 2.6 | 12.50 ± 0.49 |
| 6 | 71.58 | 11.75 | NA | 84.27 ± 1.68 | 9.17 ± 0.66 |
| 7 | 63.31 | 11.07 | NA | 52.99 ± 0.53 | 4.33 ± 0.51 |
| 8 | 68.84 | 12.95 | NA | 116.95 ± 2.3 | 12.49 ± 1.29 |

NA = not available

The results show that modified functionality is achieved with the modified psyllium of the present invention compared to the control examples. Treatment with Viscozyme L and Shearzyme L substantially lowered the gel hardness of the resultant psyllium compared to control. Increased gel hardness resulted from treatment with the Celluclat 1.5L and Pentopan Additional embodiments of the present invention will be readily apparent to those skilled in the art and are meant to be encompassed within the scope of the claims appended hereto. All references cited herein are incorporated by reference in their entireties.

Example 10

Test the cholesterol lowering effect and other effects of the enzyme modified psyllium of the present invention, studies will be conducted on male Golden Syrian hamsters. The hamsters will be divided into 3 groups of 12 (total 60) and each group was fed one of 3 semi-synthetic diets for 3 weeks, after which animals will be killed and blood lipids determined. The diets will be positive (w/cholesterol) and negative (w/out cholesterol) controls, raw psyllium, and the modified psyllium according to the invention the amount of modified psyllium in the diet was increased accordingly to make all psyllium diets identical in soluble dietary fiber content.

The test results will show that the enzymatically modified psyllium of the present invention reduced serum total cholesterol, serum LDL, and serum triglycerides.

It will be understood that the specification and examples are illustrative of the present invention and that other embodiments within the spirit and scope of the invention will suggest themselves to those skilled in the art.

It is claimed:

1. A method for producing an edible modified psyllium comprising the step of:
    adding raw psyllium to a buffered aqueous mixture comprising an enzyme, wherein said enzyme hydrolyzes at least one non-starch polysaccharide of the raw psyllium thereby forming an edible modified psyllium.

2. The method of claim 1, wherein the enzyme is selected from the group consisting of xylanases, cellulases, arabanases, hemicellulases, pentosanases, β-glucanases, and mixtures thereof.

3. The method of claim 1, wherein the enzyme is a xylanase.

4. The method of claim 1, wherein the buffer maintains the aqueous solution at a pH of from about 4.5 to about 6.

5. The method of claim 1, further comprising the step of inactivating the enzyme.

6. The method of claim 1, further comprising freeze drying the aqueous mixture.

7. The method of claim 1, wherein said raw psyllium is 98% pure, 40 mesh psyllium.

8. A pharmaceutical comprising the edible modified psyllium prepared by the method of claim 1 and at least one other edible component.

9. A food product comprising the edible modified psyllium prepared by the method of claim 1 and at least one other edible component.

10. A beverage comprising the edible modified psyllium prepared by the method of claim 1 and at least one edible liquid.

11. A drink mix comprising the edible modified psyllium prepared by the method of claim 1 and at least one other edible component.

12. A livestock feed comprising the edible modified psyllium prepared by the method of claim 1 and at least one other edible livestock feed component.

13. A bulk laxative comprising the edible modified psyllium prepared by the method of claim 1 and at least one other edible component.

14. A method of preparing an edible psyllium-containing product comprising the steps of:

a) blending raw psyllium with at least one edible ingredient to form an edible blend;

b) adding a buffered aqueous mixture comprising an enzyme to said blend, wherein said enzyme hydrolyzes at least one non-starch polysaccharide of the raw psyllium in the edible blend, thereby forming an edible psyllium-containing product.

15. The method of claim 14, further comprising the step of inactivating the enzyme.

16. A method of reducing serum cholesterol in a mammal comprising orally administering a sufficient amount of the modified psyllium prepared by the method of claim 1 to a mammal to reduce the mammal's serum cholesterol.

17. A method of reducing serum triglycerides in a mammal comprising orally administering a sufficient amount of the modified psyllium prepared by the method of claim 1 to a mammal to reduce the mammal's serum cholesterol.

18. A method of reducing serum LDL in a mammal comprising orally administering a sufficient amount of the modified psyllium prepared by the method of claim 1 to a mammal to reduce the mammal's serum LDL.

19. A method of producing a bulk laxative effect in a mammal comprising orally administering a sufficient amount of the modified psyllium prepared by the method of claim 1 to a mammal to produce bulk laxation.

* * * * *